(12) United States Patent
Spreiter et al.

(10) Patent No.: US 11,517,362 B2
(45) Date of Patent: Dec. 6, 2022

(54) SELF-RETAINING SCREW AND SCREWDRIVER

(71) Applicant: DEPUY SYNTHES PRODUCTS, INC., Raynham, MA (US)

(72) Inventors: Gregor Spreiter, Zuchwil (CH); Henri Défossez, Neuchatel (CH); Simon Scherrer, Zurich (CH); Gaser El Zoghbi, Rombach (CH); Roger Koch, Aarau (CH); Yvonne Schumacher, Solothurn (CH); Rhett Rapier, Solothurn (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 234 days.

(21) Appl. No.: 16/863,586

(22) Filed: Apr. 30, 2020

(65) Prior Publication Data
US 2021/0338296 A1 Nov. 4, 2021

(51) Int. Cl.
*A61B 17/86* (2006.01)
*A61B 17/88* (2006.01)
*A61B 34/00* (2016.01)
*A61B 90/00* (2016.01)

(52) U.S. Cl.
CPC ...... *A61B 17/8645* (2013.01); *A61B 17/8888* (2013.01); *A61B 17/8891* (2013.01); *A61B 17/8894* (2013.01); *A61B 34/76* (2016.02); *A61B 2090/062* (2016.02)

(58) Field of Classification Search
CPC ............ A61B 17/8888; A61B 17/8891; A61B 17/8894; A61B 17/8645
See application file for complete search history.

(56) References Cited

U.S. PATENT DOCUMENTS

| 2,288,584 | A | * | 6/1942 | Longfellow | ....... | A61B 17/8891 81/438 |
| 2,312,869 | A | * | 3/1943 | Boyer | ................ | A61B 17/8891 81/438 |
| 2005/0149053 | A1 | * | 7/2005 | Varieur | .............. | A61B 17/7091 606/104 |
| 2006/0079903 | A1 | | 4/2006 | Wong | | |
| 2008/0041196 | A1 | * | 2/2008 | Companioni | ......... | B25B 23/101 81/453 |

(Continued)

FOREIGN PATENT DOCUMENTS

| EP | 3 501 438 A1 | 6/2019 |
| WO | 2009/052294 A1 | 4/2009 |

*Primary Examiner* — Christian A Sevilla
(74) *Attorney, Agent, or Firm* — Fay Kaplun & Marcin, LLP

(57) ABSTRACT

A bone screw insertion device, comprises an outer sleeve extending from a proximal end to a distal end and including a channel extending therethrough and a driving member extending longitudinally through the channel of the outer sleeve from a proximal end to a distal end configured to engage a driving recess of a bone screw, the outer sleeve movable relative to the driving member between a first position in which the distal end of the outer sleeve extends over and covers a proximal portion of a bone screw engaged with the driving member, to a second position in which the distal end of the outer sleeve is longitudinally aligned with a proximal end of a bone screw engaged with the driving member.

22 Claims, 7 Drawing Sheets

(56) References Cited

U.S. PATENT DOCUMENTS

| | | | |
|---|---|---|---|
| 2008/0140086 A1* | 6/2008 | Moore | A61B 17/7091 |
| | | | 606/104 |
| 2008/0147128 A1* | 6/2008 | Fritzinger | A61B 17/862 |
| | | | 606/104 |
| 2009/0187194 A1 | 7/2009 | Hamada | |
| 2014/0276894 A1* | 9/2014 | Ramsay | A61B 17/7076 |
| | | | 606/104 |
| 2015/0272648 A1* | 10/2015 | Leonard | A61B 17/8891 |
| | | | 606/104 |
| 2017/0296245 A1* | 10/2017 | Gault | A61B 17/864 |
| 2018/0263669 A1* | 9/2018 | Peterson | A61B 17/8605 |
| 2019/0336187 A1* | 11/2019 | Zander | A61B 17/8891 |

* cited by examiner

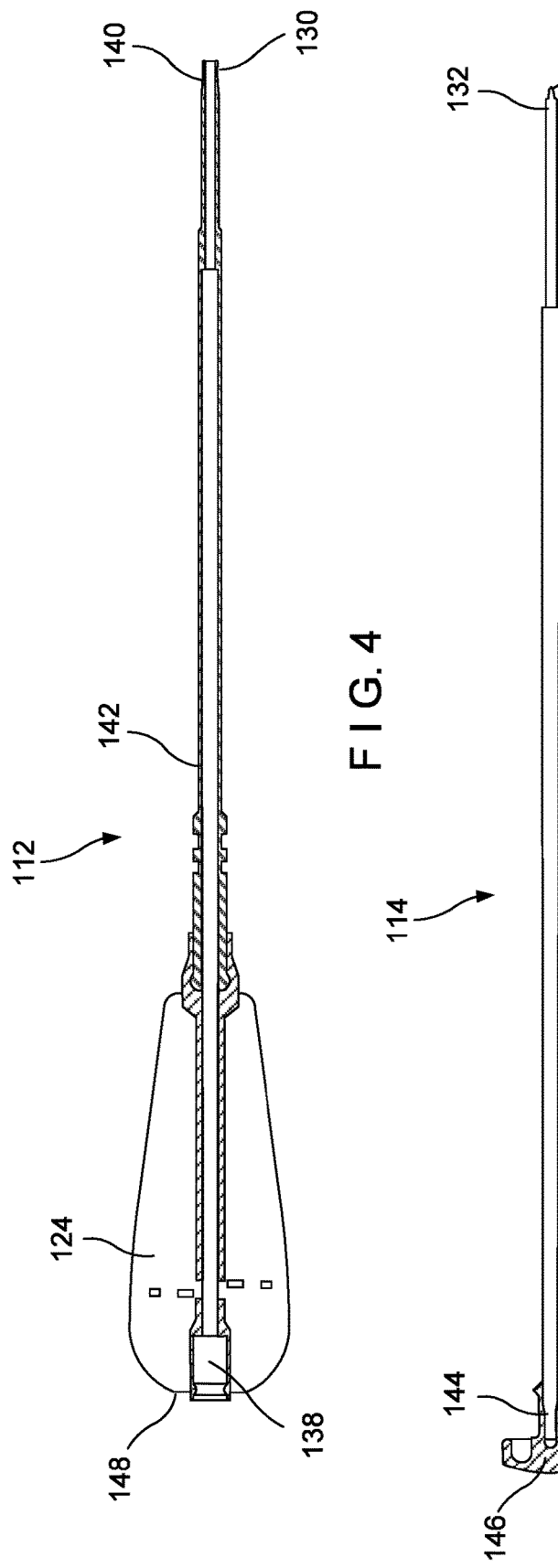 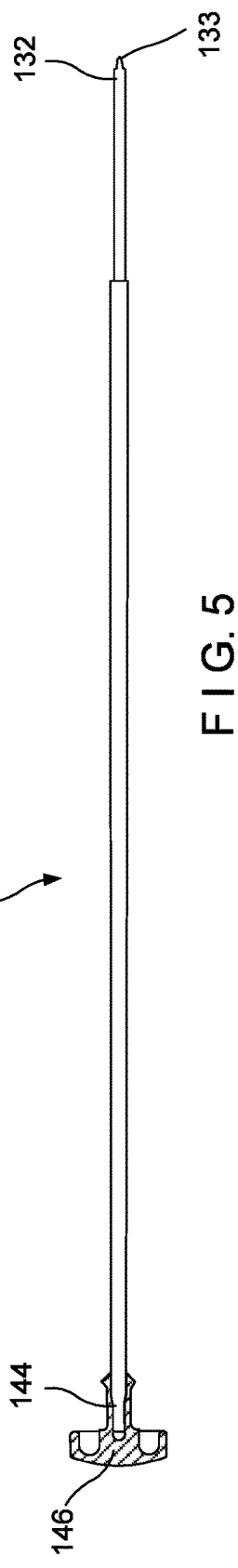 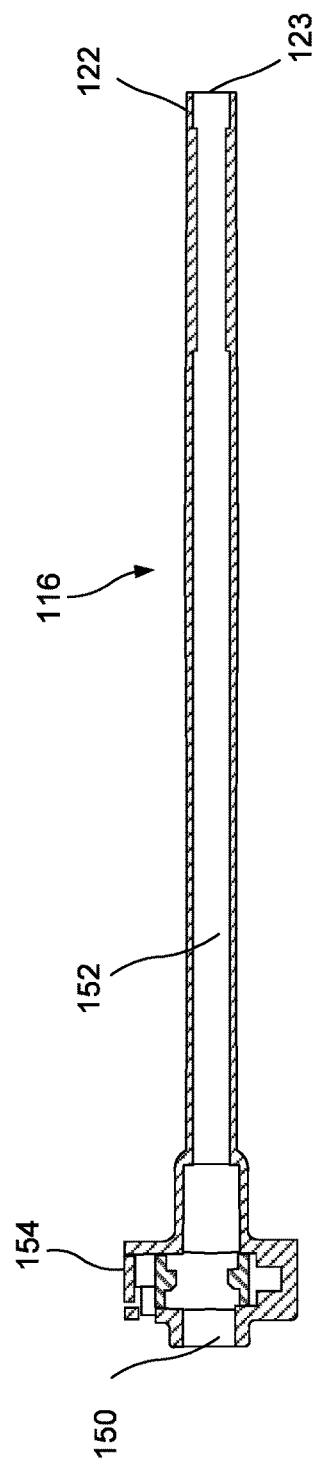
FIG. 4
FIG. 5
FIG. 6

SELF-RETAINING SCREW AND SCREWDRIVER

BACKGROUND

Some fractures of long bones may be treated by placing the bone into corrective alignment and inserting an intramedullary nail into a medullary canal of the aligned bone. The intramedullary nail may be fixed relative to the bone via fixation screws that are inserted into fixation holes that extend laterally through the intramedullary nail. Fixation screws may include, for example, headless screws (e.g., screws having a threading along an entire length thereof) which may be inserted such that the screws are flush to the bone. In some cases, however, the headless screws may be inserted too far into the bone, which may interfere with the intramedullary nail, lose purchase in a near cortex of the bone and/or protrude too far from a far cortex of the bone.

SUMMARY

The present disclosure relates to a system for treating a bone. The system includes a headless screw and an insertion device. The headless screw extends from a proximal end to a distal end and including a threading extending along an outer surface thereof. The headless screw includes a driving recess extending into the proximal end thereof. The insertion device includes an outer sleeve extending from a proximal end to a distal end and including a channel extending therethrough and a driving member. The driving member extends longitudinally through the channel of the outer sleeve from a proximal end to a distal end. The proximal end of the driving member extends proximally of the proximal end of the outer sleeve to a distal end configured to engage the driving recess of the headless screw to rotationally drive the headless screw into a bone. The outer sleeve is movable relative to the driving member between a first position, in which the distal end of the outer sleeve extends over and covers a proximal portion of the headless screw when the headless screw is engaged with the driving member in the operative configuration, to a second position, in which a distal end of the outer sleeve is longitudinally aligned with a proximal end of the headless screw.

In an embodiment, the headless screw further includes a retaining recess extending distally from the driving recess.

In an embodiment, the insertion device further includes a retaining member extending longitudinally through a channel of the driving member from a proximal end to a distal end configured to engage the retaining recess so that the headless screw is retained on the insertion device during insertion of the headless screw into the bone.

In an embodiment, the retaining recess includes a threading therealong and the distal end of the retaining member is correspondingly threaded so that, rotation of the retaining member about a longitudinal axis thereof relative to the driving member, engages the threading of the retaining member with the threading of the retaining recess to retain the headless screw on the insertion device.

In an embodiment, the proximal end of the retaining member includes a knob extending proximal of the proximal end of the driving member to rotate the retaining member relative to the driving member.

In an embodiment, the outer sleeve includes a locking mechanism for locking the outer sleeve relative to the driving member in one of the first and second positions, the locking mechanism including a locking tab biased toward a locking configuration via a biasing element and a push button compressing the biasing element to move the locking tab toward an unlocked configuration.

In an embodiment, the driving member includes a first groove extending into an outer surface of the driving member so that when the locking tab is received within the first groove the outer sleeve is in the first position relative to driving member, and a second groove extending into the outer surface of the driving member proximal of the first groove so that when the locking tab is received within the second groove the outer sleeve is in the second position relative to the driving member.

In an embodiment, a core diameter of the proximal portion of the headless screw is larger than a core diameter along a remaining portion of the headless screw.

In an embodiment, the outer sleeve includes gripping features extending distally from the distal end thereof, the gripping features configured to engage the bone.

In an embodiment, the outer sleeve includes a threading along the distal end thereof configured to engage a corresponding threading along the proximal portion of the headless screw.

In an embodiment, the outer sleeve includes a proximal portion and a distal portion connected to one another via a friction interface, the distal portion being rotatable about a longitudinal axis thereof.

In an embodiment, the proximal portion of the outer sleeve includes a mating feature configured to mate with a corresponding mating feature on the driving member to prevent the proximal portion from rotating relative to the driving member.

In an embodiment, the proximal portion of the outer sleeve includes a depth indicator that indicates a depth to which the headless screw has been inserted into the bone. In addition, the present disclosure relates to a bone screw insertion device. The device includes an outer sleeve extending from a proximal end to a distal end and including a channel extending therethrough and a driving member. The driving member extends longitudinally through the channel of the outer sleeve from a proximal end to a distal end configured to engage a driving recess of a bone screw. The outer sleeve is movable relative to the driving member between a first position in which the distal end of the outer sleeve extends over and covers a proximal portion of a bone screw engaged with the driving member, to a second position in which the distal end of the outer sleeve is longitudinally aligned with a proximal end of a bone screw engaged with the driving member.

In an embodiment, the system further includes a retaining member extending longitudinally through the channel of the driving member from a proximal end to a distal end, the retaining member being configured to releasably engage a retaining recess of a bone screw.

In an embodiment, the distal end of the retaining member is threaded to engage a corresponding threading of the retaining recess.

In an embodiment, the proximal end of the retaining member includes a knob extending proximal of the proximal end of the driving member to rotate the retaining member relative to the driving member.

In an embodiment, the outer sleeve includes a locking mechanism for locking the outer sleeve relative to the driving member in one of the first and second positions, the locking mechanism including a locking tab biased toward a locking configuration via a biasing element and a push button compressing the biasing element to move the locking tab toward an unlocked configuration.

In an embodiment, the driving member includes a first groove extending into an outer surface of the driving member so that when the locking tab is received within the first groove the outer sleeve is in the first position relative to driving member, and a second groove extending into the outer surface of the driving member proximal of the first groove so that when the locking tab is received within the second groove the outer sleeve is in the second position relative to the driving member.

In an embodiment, the outer sleeve includes gripping features extending distally from the distal end thereof, the gripping features configured to engage the bone.

In an embodiment, the outer sleeve includes a threading along an inner surface of a distal portion thereof configured to engage a corresponding threading along the proximal portion of a headless screw received within the outer sleeve.

In an embodiment, the outer sleeve includes a proximal portion and a distal portion connected to one another via a friction interface, the distal portion of the outer sleeve being rotatable about a longitudinal axis thereof relative to the proximal portion of the outer sleeve.

In an embodiment, the proximal portion of the outer sleeve includes a mating feature configured to mate with a corresponding mating feature on the driving member to prevent the proximal portion from rotating relative to the driving member.

In an embodiment, the proximal portion of the outer sleeve includes a depth indicator that indicates a depth to which the headless screw engaged to the driving member has been inserted into the bone. Furthermore, the present disclosure relates to a method for implanting a bone screw which includes assembling a headless bone screw with an insertion device by inserting a distal end of a driving member of the insertion device into a correspondingly sized and shaped driving recess of the headless screw; inserting the headless bone screw to a position adjacent to a target area of the bone with the insertion device in a first position with an outer sleeve mounted over the driving member so that a distal end of the outer sleeve extends over and covers a proximal portion of the headless screw; driving the headless bone screw into the bone by rotating the driving member until the distal end of the outer sleeve abuts a near cortex of the bone; drawing the outer sleeve proximally relative to the driving member from the first position to a second position in which a distal face of the outer sleeve is longitudinally aligned with a proximal face of the headless bone screw; and driving the headless bone screw further distally into the bone until the distal end of the outer sleeve contacts the near cortex of the bone, providing tactile feedback to the user that the headless screw is flush with the bone.

In an embodiment, the method further includes retaining the headless bone screw on the insertion device by threadedly engaging a threaded distal portion of a retaining member with a correspondingly threaded retaining recess of the headless bone screw, the retaining member extending longitudinally through the driving member.

In an embodiment, drawing the outer sleeve proximally relative to the driving member from the first position to the second position includes moving a locking mechanism of the outer sleeve from a locked configuration to an unlocked configuration so that a locking tab of the locking mechanism is movable from a first groove along the driving member to a second groove along the driving member.

In an embodiment, the locking tab is biased toward the locked configuration via a biasing.

In an embodiment, moving the locking mechanism from the locked configuration to the unlocked configuration includes pressing a push button to compress the biasing element so that the locking tab is disengaged from the first groove and the outer sleeve is proximally movable along the driving member, the locking tab reverts to the biased configuration to engage the second groove in the second configuration.

In an embodiment, the method further includes removing the insertion device from the implanted headless bone screw by disengaging the threaded distal portion of the retaining member from retaining recess and drawing the insertion device proximally therefrom.

In an embodiment, the method further includes retaining the headless bone screw on the insert device by threadedly engaging the distal end of the outer sleeve with the proximal portion of the headless screw.

In an embodiment, the outer sleeve includes a proximal portion and a distal portion connected via a friction interface, the distal portion being rotatable about a longitudinal axis thereof, such that, the distal portion correspondingly rotates along with the driving member relative to the proximal portion of the outer sleeve.

In an embodiment, when the distal end abuts the near cortex of the bone, the friction interface provides a feedback indicating that the proximal portion of the headless screw is driving into the bone.

BRIEF DESCRIPTION

FIG. 4 shows a longitudinal cross-sectional view of a driving member of the insertion device according to the system of FIG. 1;

FIG. 5 shows a side view of a retaining member of the insertion device according to the system of FIG. 1;

FIG. 6 shows a longitudinal cross-sectional view of an outer sleeve of the insertion device according to the system of FIG. 1;

DETAILED DESCRIPTION

Figure 1:
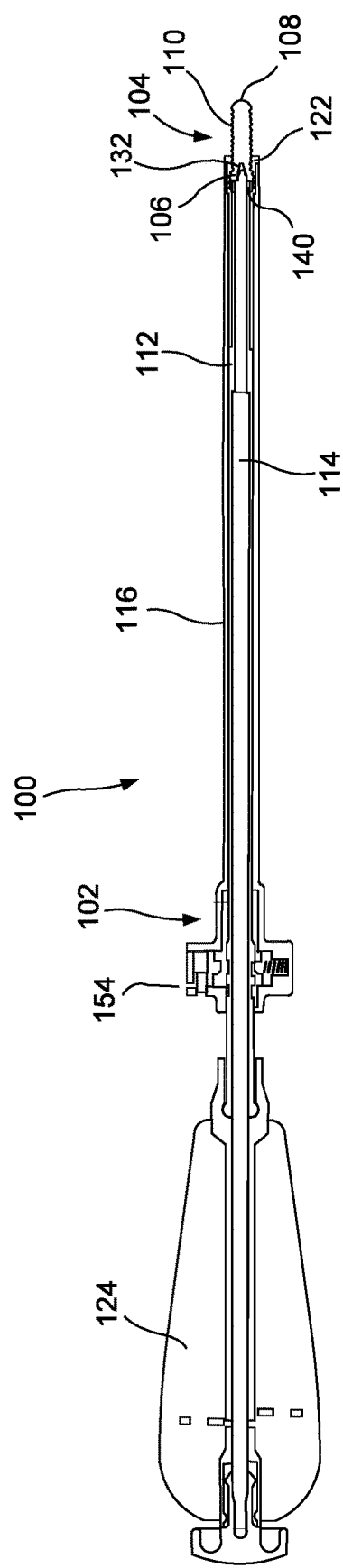
FIG. 1 shows a longitudinal cross-sectional view of a system according to an exemplary embodiment of the present disclosure.

The present disclosure may be further understood with reference to the following description and the appended drawings, wherein like elements are referred to with the same reference numerals. The present embodiments relate to the treatment of a bone and, in particular, to the treatment of fractures of long bones such as the femur, tibia, humerus, etc. Once the bone is placed into corrective alignment, an intramedullary nail is inserted through a medullary canal of the bone and fixed relative thereto via fixation screws. In particular, headless screws, which include a threading along an entire length thereof, may be inserted through fixation openings extending laterally through the intramedullary nail so that the headless screws are flush to the bone.

In some cases, however, headless screws can be inserted too far into the bone, which may cause the screw to interfere with the intramedullary nail, lose purchase in the near cortex, and/or protrude too far from the far cortex. The exemplary embodiments describe a system including an insertion device for a headless screw, which provides a tactile feedback to a user when the screw is flush to the bone, preventing the screw from being inserted too far into the bone. It will be understood by those of skill in the art that the terms proximal and distal, as used herein refer to a direction toward (proximal) and away from (distal) a user of the system described herein. It will be further understood that, although the embodiments described herein are directed to an intramedullary nail system for long bones, the insertion device and headless screw of the present disclosure may also be utilized for other bone fixation systems in which a headless screw should be inserted flush to the bone.

As shown in FIGS. 1-10, a system 100 for treating a bone comprises an insertion device 102 for inserting a headless screw 104 flush to a bone 10. The headless screw 104 extends longitudinally from a proximal end 106 to a distal end 108 and includes a threading 110 along an entire length thereof. The insertion device 102 may include a driving member 112 for driving the headless screw 104 into the bone 10, a retaining member 114 for engaging and retaining the headless screw 104 as the headless screw 104 is being driven into the bone 10, and an outer sleeve 116 for providing a tactile feedback to a user (e.g., a surgeon), when the proximal end 106 of the headless screw 104 is flush to the bone. Each of the driving member 112, retaining member 114 and the outer sleeve 116 are coupled to a handle member 124 so that the driving member 112, retaining member 114 and the outer sleeve 116 are movable relative to one another to insert the headless screw 104 into the bone, as will be described in further detail below.

Figure 3:
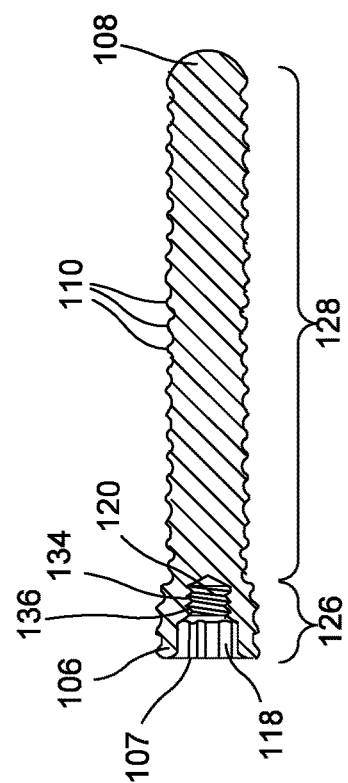
FIG. 3 shows a longitudinal cross-sectional view of the headless screw according to the system of FIG. 1.
Figure 2:
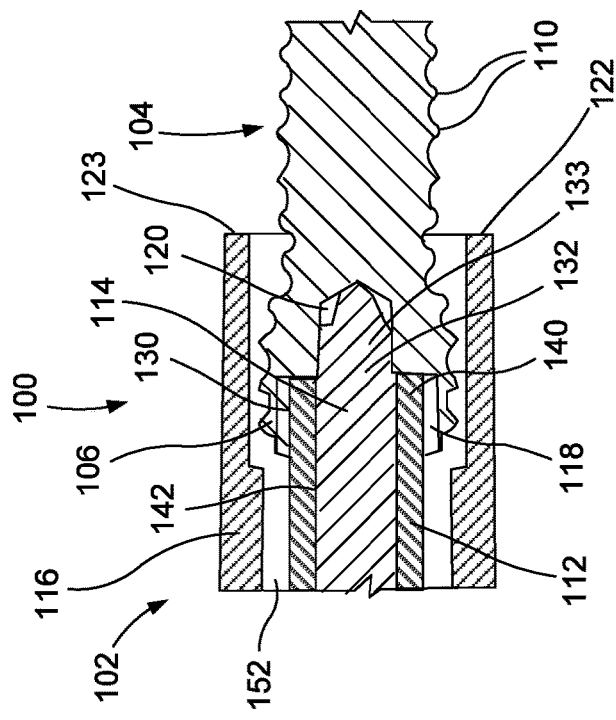
FIG. 2 shows an enlarged view of a distal portion of an insertion device and a proximal portion of a headless screw according to the system according to FIG. 1.

As shown in FIG. 3, the headless screw 104 extends along a longitudinal axis from the proximal end 106 to the distal end 108. The threading 110 extends along an entire length of the headless screw 104 so that the headless screw 104 is insertable into the bone 10 such that the proximal end 106 is flush with a near cortex of the bone 10. In some embodiments, a proximal portion 126 of the headless screw 104 may have a larger core diameter and/or a larger threaded diameter than a remaining portion 128 of the headless screw 104. A larger core diameter and outer diameter along the proximal portion 126 will increase an insertion torque as the headless screw 104 is being screwed (e.g., rotated) into the bone providing further tactile feedback to the user that the proximal portion 126 of the headless screw 104 is engaging the bone 10. It will be understood by those of skill in the art that the core diameter of the proximal portion 126 may be defined via an exterior surface of the proximal portion 126 along which threads do not extend and/or via radially inner ends of the threads extending along the proximal portion 126.

The proximal end 106 of the headless screw 104 includes a driving recess 118, which extends distally into the proximal end 106 of the headless screw 104 along the longitudinal axis of the headless screw 104. As shown in FIG. 3, the driving recess 118 is configured to receive a correspondingly sized and shaped engaging portion 130 of the driving member 112 of the insertion device 102. The driving recess 118 is configured so that, when the engaging portion 130 of the driving member 112 is received therewithin and rotated about a longitudinal axis thereof, a torsional force is applied to the headless screw 104 to drive the headless screw 104 into the bone 10.

In one embodiment, the driving recess 118 includes a substantially circular central portion and a plurality of notches formed along a surface of the substantially circular central portion so that the notches extend radially outward from a longitudinal axis of the headless screw 104. It will be understood by those of skill in the art that the driving recess 118 may include any number of notches in any of a variety of configurations so long as the notches are sized and shaped to engage corresponding portions of the engaging portion 130 of the driving member 112. It will also be understood by those of skill in the art, that the driving recess 118 may have any of a variety of configurations so long as the driving recess 118 is engageable with the driving member 112.

For example, in another embodiment, the driving recess 118 may have a hexagonal cross-section. In another example, the driving recess 118 may be star shaped. It will be understood by those of skill in the art, however, that the driving recess 118 may have any of a variety of shapes so long as a torsional force may be applied to the headless screw 104 thereby.

The proximal end 106 of the headless screw 104 also includes a retaining recess 120 extending distally from the driving recess 118. The retaining recess 120 has a smaller cross-sectional area than the driving recess 118 and is configured to receive a threaded retaining portion 133 at a distal end 132 of the retaining member 114. In one embodiment, the retaining recess 120 may include a threading 134 along an interior surface 136 thereof for engaging a correspondingly threaded engaging portion 133 of the retaining member 114. As will be described in further detail below, engagement between the retaining member 114 and the retaining recess 120 aids in retaining (e.g., holding) the headless screw 104 to the insertion device 102 while the headless screw 104 is being driven into the bone 10.

As described above, the insertion device 102 includes the driving member 112, the retaining member 114 and the outer sleeve 116. As shown in FIG. 4, the driving member 112 extends longitudinally from a proximal end 138 to the engaging portion 130 at a distal end 140 thereof, and includes a channel 142 extending longitudinally therethrough. The proximal end 138 is connected to the handle member 124 so that, when the handle member 124 is rotated about a longitudinal axis of the insertion device 102, the driving member 112 is correspondingly rotated to drive a headless screw 104 engaged to the engaging portion 130 into the bone 10, as will be described in further detail below. Although the driving member 112 is shown and describes as including the handle member 124 at the proximal end 138, in another embodiment, the proximal end 138 may be configured so that the proximal end 138 may be coupled to one of the handle member 124 and a power driver so that the headless screw 104 may be manually driven or power driven into the bone, as desired.

As shown in FIG. 5, the retaining member 114 extends longitudinally from a proximal end 144 to the distal end 132 and is sized and shaped to be received within the channel 142 of the driving member 112. In one embodiment, as described above, the distal end 132 include the threaded retaining portion 133 configured to engage the corresponding threading 134 of the retaining recess 120 of the headless screw 104. The proximal end 144 of the retaining element 114 may be attached to, for example, a knob 146 which, when the retaining member 114 is received within the channel 142, extends proximally of a proximal end 148 of the handle member 124.

The retaining element 114 is longitudinally movable relative to the driving member 112 between a non-retaining configuration and a retaining configuration. In the non-retaining configuration, the distal end 132 of the retaining member 114 is flush with or proximal of the distal end 140 of the driving member 112 so that the distal end 132 of the retaining member 114 does not extend distally past the distal end 140 of the driving member 112. Thus, even when the driving member 112 is engaged with the driving recess 118 of the headless screw, the distal end 132 of the retaining member 114 does not engage the retaining recess 120 when in the non-retaining configuration. The retaining member 114, however, may be moved distally relative to the driving member 112 toward the retaining configuration, in which the distal end 132 of the retaining member 114 extends distally past the distal end 140 of the driving member 112 to engage the retaining recess 120 of the headless screw 104.

Where the distal end 132 includes the threaded retaining portion 133, the retaining member 114 may be rotated in a first direction about a longitudinal axis thereof to engage the threaded engaging portion 133 with the correspondingly threading 134 of the retaining recess 120. The retaining member 114 may be rotated via, for example, the knob 146. To move the retaining member 114 from the retaining configuration to the non-retaining configuration, the retaining member 114 is rotated about the longitudinal axis thereof in a second direction, opposite the first direction, until the threaded retaining portion 133 is unthreaded from the retaining recess 120.

As shown in FIG. 6, the outer sleeve 116 extends longitudinally from a proximal end 150 to a distal end 122 and includes a channel 152 extending longitudinally therethrough. The outer sleeve 116 is slidably mounted over the driving member 112 so that the outer sleeve 116 is longitudinally movable relative to the driving member 112 between a first position and a second position. In the first position, the distal end 122 of the outer sleeve 116 extends distally beyond the distal end 140 of the driving element 112 so that the distal end 122 extends over and covers the proximal portion 126 of the headless screw 104, when the driving recess 118 of the headless screw 104 is engaged with the engaging portion 130 of the driving member 112. In the second position, the outer sleeve 116 is drawn proximally relative to the driving member 112 so that the distal end 122 is aligned with the proximal end 106 of the headless screw 104. In particular, a distal face 123 of the distal end 122 is longitudinally aligned with a proximal face 107 of the proximal end 106 of the headless screw 104.

The headless screw 104 is initially inserted into a living body with the outer sleeve 116 in the first position until it reaches a target area of the bone 10 into which the headless screw 104 is to be driven. The headless screw 104 is inserted into the body with the proximal portion 126 covered to protect surrounding tissue from the threading 110 extending along the proximal portion 126 which acts as cutting flutes during implantation of the headless screw 104. Upon reaching the target area, the outer sleeve 116 is retracted to the second position and the headless screw 104 is driven into the bone 10 until the distal face 123 of the outer sleeve 116 abuts the near cortex of the bone 10. A distance by which the outer sleeve 116 is retracted, from the first position to the second position, corresponds to a length of the proximal portion 126 of the headless screw 104. Thus, when the headless screw 104 is driven into the bone 10 and the distal face 123 abuts the near cortex of the bone 10, the abutment between the outer sleeve 116 and the bone 10 provides tactile feedback to the user indicating that the proximal end 106 is flush with the bone 10.

Figure 7:
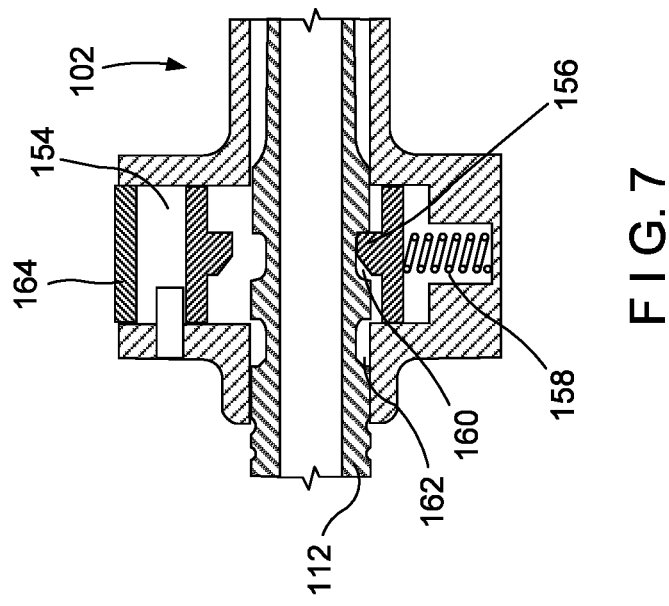
FIG. 7 shows an enlarged cross-sectional view of a locking mechanism of the outer sleeve of the insertion device according to the system of FIG. 1.

The outer sleeve 116 of this embodiment is be movable between the first and second positions via a locking mechanism 154 including a locking tab 156 biased toward a locking configuration via a biasing element 158, as shown in FIG. 7, although those skilled in the art will understand that any mechanism which permits the desired relative movement may be employed. In the locking configuration, the locking tab 156 extends into the channel 152 of the outer sleeve 116 to engage one of a first groove 160 and a second groove 162 along an exterior surface of the driving member 112. When the locking tab 156 is received within the first groove 160, the outer sleeve 116 is in the first position relative to the driving member 112. When the locking tab 156 is in the second groove 162, which is positioned proximally of the first groove 160, the outer sleeve 116 is in the second position relative to the driving member 112.

The locking tab 156 may be moved between the first and second grooves 160, 162 by, for example, a push button 164 which, when pressed, moves the locking tab 156 out of the channel 152 and out of engagement with one of the grooves 160, 162 toward an unlocked configuration. Thus, when it is desired to move the outer sleeve 116 between the first and second positions, the user may simply press the push button 164 and slide the outer sleeve 116 longitudinally proximally or distally relative to the driving member 112. When the locking tab 156 is adjacent the other of the first and second grooves 160, 162, the locking tab 156 will revert to its biased locking configuration snapping into engagement the other one of the first and second grooves 160, 162.

Although the locking mechanism 154 is shown positioned at the proximal end 150 of the outer sleeve 116, it will be understood by those of skill in the art that the locking mechanism 154 may be positioned anywhere along a length of the outer sleeve 116 so long as the locking mechanism 154 is accessible to a user during the implantation procedure and so long as the locking tab 156 may be received within the first and second grooves 160, 162 to move the outer sleeve 116 relative to the driving member 112 between the first and second positions.

It will also be understood by those of skill in the art that, if so desired, the user may press the button 164 to slide the outer sleeve 116 proximally relative to the driving member 112 to remove the outer sleeve 116 from the insertion device 102. It may be desired to remove the outer sleeve 116 for cases in which it is desired to implant the headless screw 104 distally beyond the near cortex of the bone 10. It will be understood by those of skill in the art that the outer sleeve 116 may also be removed to drive conventionally shaped bone screws including a head. The head of the conventional bone screw may include both a driving recess and a retaining recess, substantially similar to the driving recess 118 and the retaining recess 120 described above.

According to an exemplary method of the present disclosure, the insertion device 102 is coupled to the headless screw 104 by inserting the engaging portion 130 of the driving member 112 into the driving recess 118 at the proximal end 106 of the headless screw 104 and engaging the distal end 132 of the retaining member 114 with the retaining recess 120 of the headless screw 104. In one embodiment, upon inserting the engaging portion 130 of the driving member 112 into the driving recess 118 of the headless screw 104, the threaded portion 133 of the retaining member 114 is engaged with the retaining recess 120 by rotating the retaining member about the longitudinal axis thereof in the first direction and distally therealong, relative to the driving member 112 and the headless screw 104, so that the threaded retaining portion 133 threadedly engages the threading 134 of the retaining recess 120.

Figure 8:
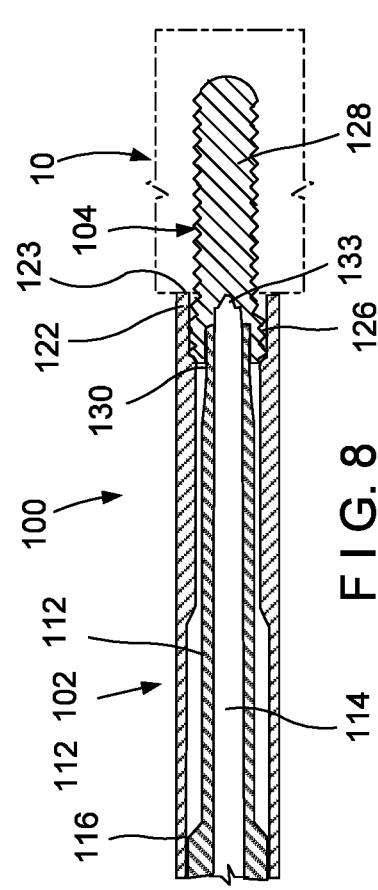
FIG. 8 shows a longitudinal cross-sectional view of a portion of the system of FIG. 1, with a distal portion of the headless screw inserted into a bone.

The headless screw 104 is initially driven into the bone 10 with the outer sleeve 116 in the first position—i.e., with the distal end 122 extending over and covering the proximal portion 126 of the headless screw 104. The headless screw 104 is driven into the bone 10 by rotating the driving member 112 about the longitudinal axis thereof until the distal end 122 of the outer sleeve 122 contacts the near cortex of the bone 10, as shown in FIG. 8, providing a first tactile feedback to the user, which indicates that the distal portion 128 of the headless screw 104 has been inserted into the bone 10 to a desired initial depth (e.g., until a distal end of the proximal portion of the screw 104 is adjacent to the near cortex of the bone).

Figure 9:
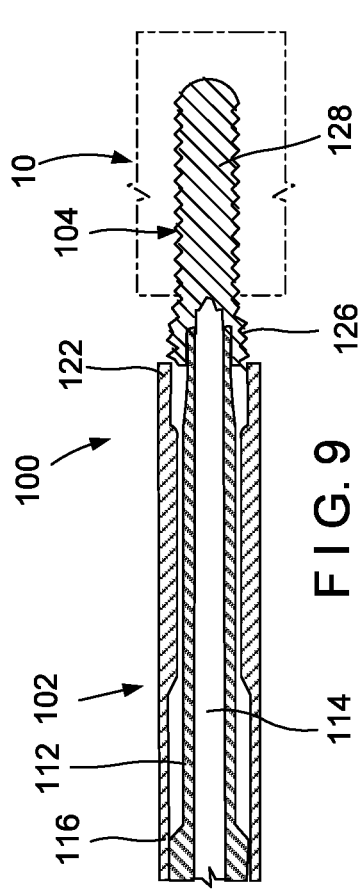
FIG. 9 shows a longitudinal cross-sectional view of a portion of the system of FIG. 1, the outer sleeve moved from a first position to a second position.

The user then moves the outer sleeve 116 proximally relative to the driving member 112 to the second position, as shown in FIG. 9, so that the distal face 123 of the outer sleeve 116 is aligned with the proximal face 107 of the headless screw 104. As described above, the outer sleeve 116 may then be locked in the second position relative to the driving member 112 via the lock mechanism 154. In one embodiment, the user may know that the distal portion 128 of the screw 104 has been fully inserted into the bone, after a predetermined number of full rotations of the headless screw 104 have been completed. For example, it may be known that two full turns of the headless screw 104 will result in a complete insertion of the distal portion 128 of the headless screw 104 into the bone 10—i.e., the screw 104 has been inserted to the point at which the distal end of the proximal portion 126 of the screw 104 is adjacent to the near cortex of the bone 10).

Figure 10:
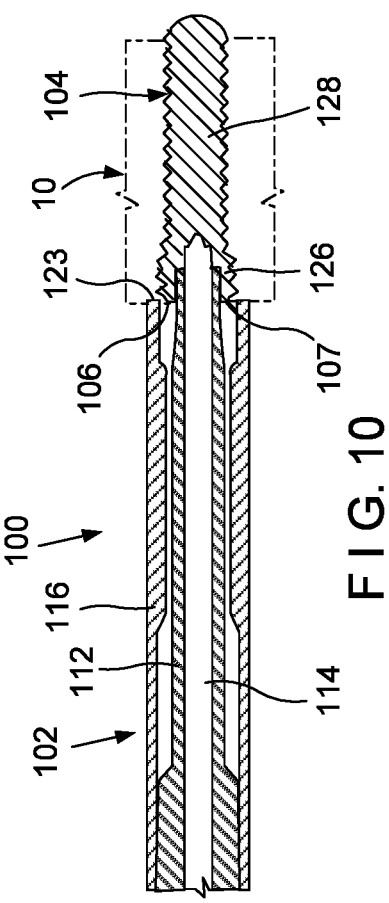
FIG. 10 shows a longitudinal cross-sectional view of a portion of the system of FIG. 1, the headless screw inserted into the bone in a desired configuration.

Once the outer sleeve 116 is fixed in the second position, the headless screw 104 is further driven into the bone 10 until the distal face 123 once again abuts the near cortex, as shown in FIG. 10, indicating to the user, via a second tactile feedback that the headless screw 104 has been inserted into the bone 10 so that the proximal end 106 is flush with the near cortex. Where the predetermined number of turns for completing insertion of the headless screw 104 is known, the second tactile feedback may provide confirmation to the user that the proximal face 107 of the headless screw 104 is flush with the surface of the near cortex.

Once the headless screw 104 has been completely inserted into the bone 10, as described above, the insertion device 102 is disengaged from the headless screw 104 and removed from the body, leaving the headless screw 104 implanted in the bone 10, as desired. In particular, the retaining member 114 is disengaged from the headless screw 104 by rotating the retaining member 114 about the longitudinal axis thereof in the second direction, until the threaded retaining portion 133 has been completely unthreaded from the retaining recess 120. The driving member 112 may then be disengaged from the driving recess 118 by simply withdrawing the insertion device 102 proximally from the headless screw 104.

Figure 12:
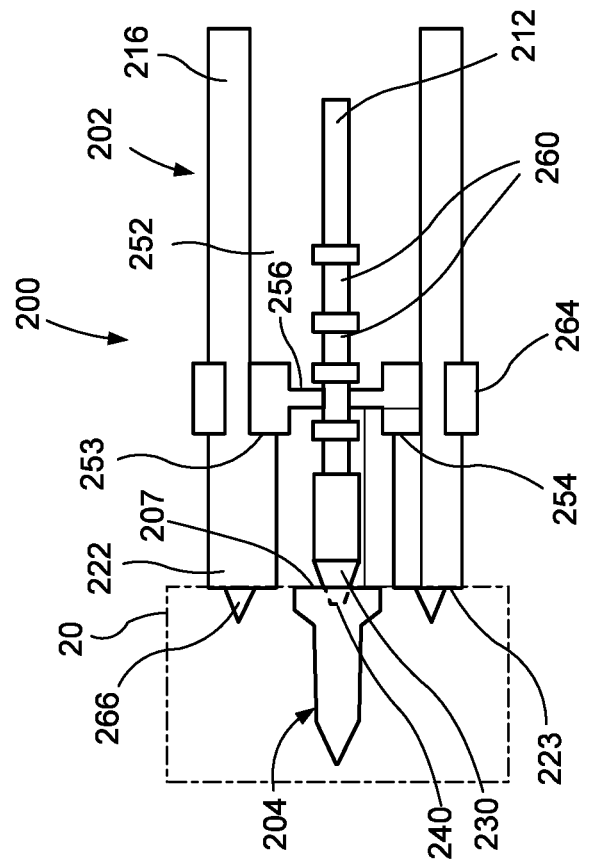
FIG. 12 shows a longitudinal cross-sectional view of the system of FIG. 11, in a second position.
Figure 11:
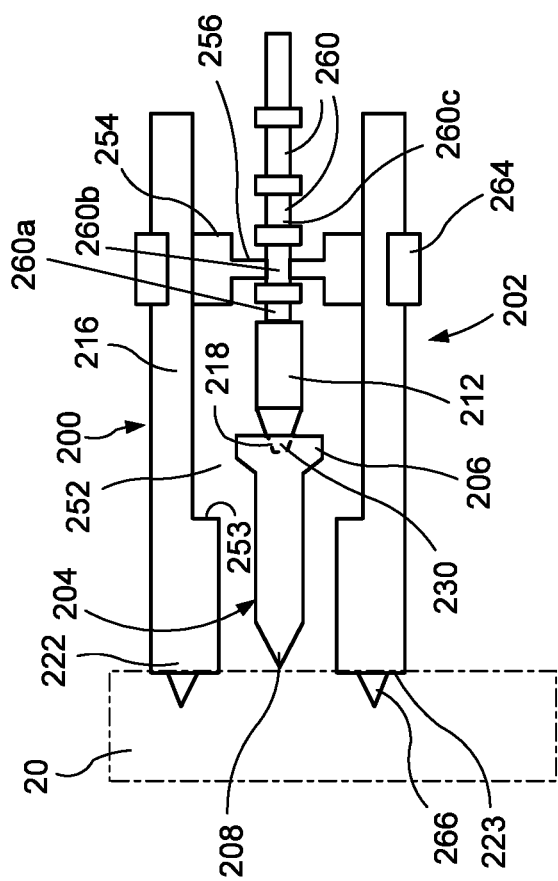
FIG. 11 shows a longitudinal cross-sectional view of a portion os a system according to another exemplary embodiment of the present disclosure, in a first position.
Figure 13:
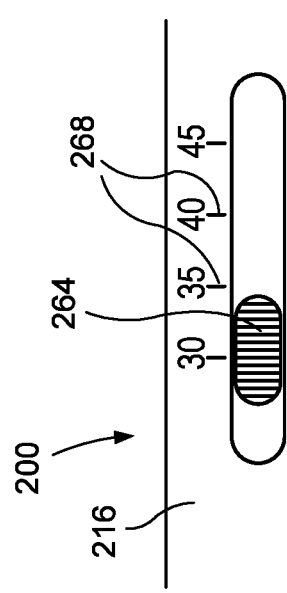
FIG. 13 shows a side view of an outer sleeve according to the system of FIG. 11.

A system 200 for inserting a headless screw 204 into a bone 20 is shown in FIGS. 11-13. As described above, the system 200 facilitates insertion of the screw 204 to a desired position, for example, with a proximal end 206 of the headless screw 204 flush with a near cortex of the bone 20. The system 200 may be substantially similar to the system 100 comprising an insertion device 202 including an outer sleeve 216 and a driving member 212 longitudinally slidable therewithin. Although not shown, it will be understood by those of skill in the art that the insertion device 202 may also include a retaining member substantially similar to the retaining member 114, for retaining the headless screw 204 during insertion thereof into the bone. Similarly to the insertion device 102, the outer sleeve 216 is longitudinally movable relative to the driving member 212 between a first initial position, as shown in FIG. 11, and a second position, as shown in FIG. 12, which indicates to a user that the headless screw 204 has been inserted into the bone 20 in the desired position—e.g., so that the proximal end 206 is flush with the bone 20.

In this embodiment, however, in the first position, the outer sleeve 216 extends over and covers an entire length of the headless screw 204 so that a position of the outer sleeve 216 relative to the driving member 212 in the first position is based on a selected length of the headless screw 204. Thus, prior to insertion of the headless screw 204 into the bone, the user may select a headless bone screw 204 having a desired length and adjust the outer sleeve 216 to a desired first position corresponding to the length of the selected headless bone screw 204, as will be described in further detail below.

The headless bone screw 204 may be substantially similar to the bone screw 104 extending longitudinally from the proximal end 206 to the distal end 208 and including a threading extending along an entire length thereof. The headless screw 204 also includes a driving recess 218 extending into the proximal end 206, the driving recess 218 being sized, shaped and configured to engage a correspondingly sized and shaped engaging portion 230 of the driving member 212. The headless screw 204 may also include a retaining recess (not shown) substantially similar to the retaining recess of the headless screw 104.

As described above, the insertion device 202 comprises the outer sleeve 216 and the driving member 212 slidably housed therewithin. The outer sleeve 216 may be substantially similar to the outer sleeve 116, extending from a proximal end to a distal end 222 and including a channel 252 extending therethrough. The channel 252, however, includes a shoulder 253 positioned along a distal portion thereof so that, as will be described in further detail below, the shoulder 253 acts as a stop to prevent further distal movement of the driving member 212 once the driving member 212 is in the second position relative to the outer sleeve 216. A distal face 223 of the outer sleeve 216 may also include a plurality of teeth 266 protruding therefrom and configured to engage the bone 20 when the distal face 223 is pressed thereagainst. The teeth 266 hold the insertion device 202 in a target position along the bone 20 so that the headless screw 204 may be driven thereinto.

The driving member 212 may be substantially similar to the driving member 112 extending from a proximal end to a distal end 240 including the engaging portion 230 sized, shaped and configured to engage the driving recess 218 of the headless screw 204. The driving member 212, in this embodiment, however, further includes a plurality of grooves 260 extending longitudinally along a distal portion thereof. Each of the grooves 260 extends about a circumference of the driving member and is configured to receive a locking tab 256 of a locking mechanism 254, as will be described in further detail below, for fixing the outer sleeve 216 and the driving member 212 in a desired first position relative to one another. Each groove 260 defines a selected length of the headless screw 204. For example, a first groove 260a may represent a 30 mm screw, a second, immediately proximal groove 260b may represent a 35 mm and a third groove 260c immediately proximal the second groove 260b may represent a 40 mm screw, etc.

The locking mechanism 254 may, in this embodiment, include a sliding push button 264 slidable along a length of the outer sleeve 216 and relative to the driving member 212 so that a locking tab 256 thereof may engage a desired one of the grooves 260 of the driving member 212. Similarly to the locking tab 156, the locking tab 256 may be biased toward a locking configuration via a biasing element such as a spring. Thus, when the push button 264 is pressed, the biasing element is compressed to disengage the locking tab 256 toward an unlocked configuration so that by also sliding the push button 264 along a length of the outer sleeve 216, the locking tab 256 may be moved to a desired position therealong, as shown in FIG. 13, corresponding to a desired one of the grooves 260. The push button 264 may then be released so that the locking tab 256 reverts to its biased configuration and engages a desired one of the grooves 260 corresponding to the selected length of the headless screw 204. In this embodiment, the outer sleeve 216 includes markings 268 therealong to indicate positions corresponding to the desired lengths of the headless screw 204.

Once a length of the headless screw 204 has been selected and the push button 264 has been adjusted to fix the outer sleeve 216 and the diving member 212 in the corresponding first position, the headless screw 205 may be inserted into the bone. The engaging portion 230 of the driving member 212 is inserted into the driving recess 218 so that, in the first position, the outer sleeve 216 extends over and covers an entire length of the headless screw 204. In one embodiment, a distal tip of the headless screw 204 and the distal face 223 of the outer sleeve 216 are longitudinally aligned in the first position. The insertion device 202 is then pressed distally against a target portion of the bone 20 so that the teeth 266 along the distal face 223 of the outer sleeve 216 engages the bone 20.

Once in this target position, the driving member 212 is rotated about a longitudinal axis thereof, relative to the outer sleeve 216, and moved distally relative thereto so that the headless screw 204 is driven out of the outer sleeve 216 and into the bone 20. The headless screw 204 may be driven into the bone 20 until a portion of the locking mechanism 254 abuts the shoulder 253, indicating to the user that the driving member 212 and the outer sleeve 216 are in the second position relative to one another—i.e., the headless screw 204 is in the desired configuration within the bone 20, in which the proximal face 207 of the headless screw 204 is flush with a near cortex of the bone.

Figure 14:
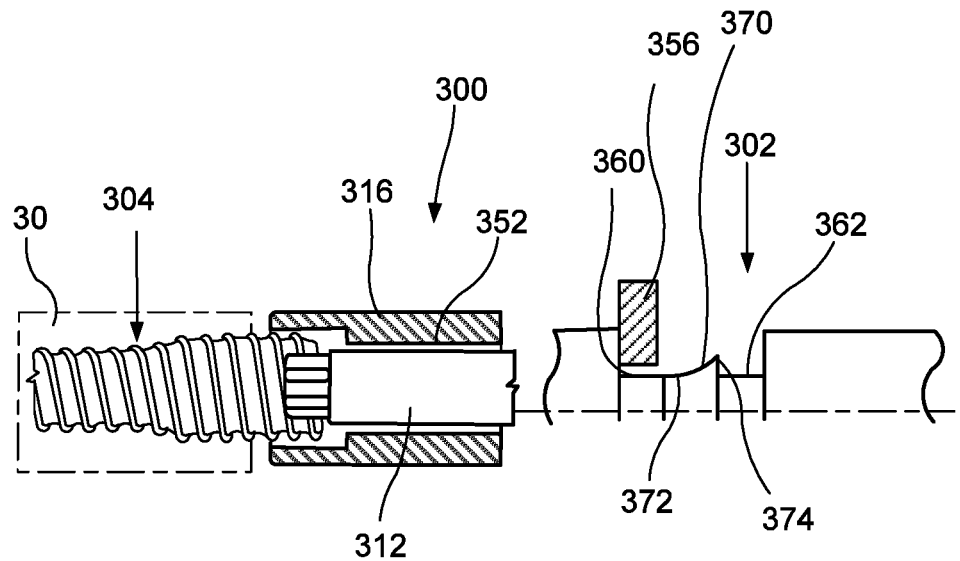
FIG. 14 shows a partial longitudinal cross-sectional view of a portion of a system according to another exemplary embodiment of the present disclosure, in a first position.
Figure 15:
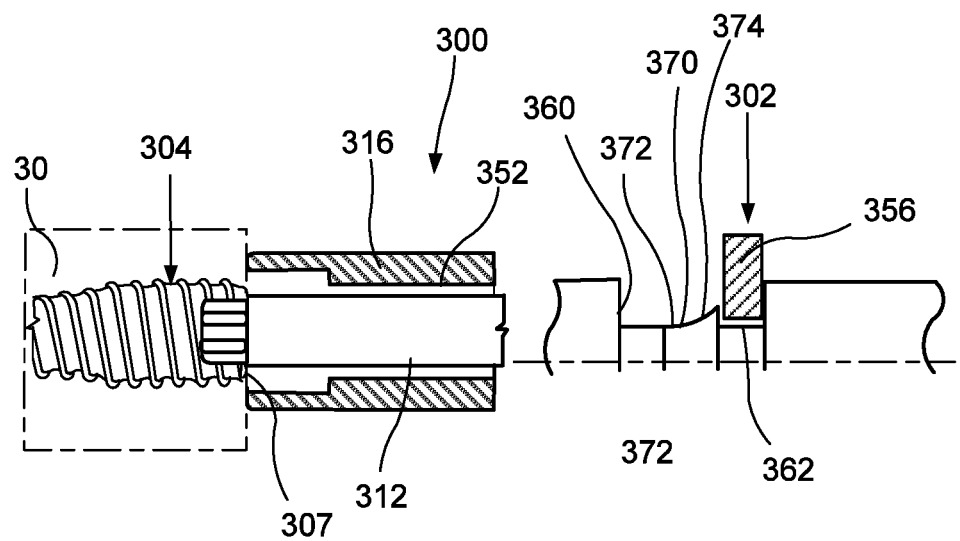
FIG. 15 shows a partial longitudinal cross-sectional view of the portion of the system of FIG. 14, in a second position.

As shown in FIGS. 14-17, a system 300 may be substantially similar to the systems 100, 200, as described above, comprising an insertion device 302 for inserting a headless screw 304 to a desired position within a bone 30 (e.g., with a proximal face 307 of the headless screw 304 substantially flush with a surface of a near cortex of the bone 30). Similarly to the systems described above, the insertion device 302 includes an outer sleeve 316 within which a driving member 312 is longitudinally movable between a first initial position, as shown in FIG. 14, and a second position, as shown in FIG. 15, which indicates to a user that the headless screw 304 is in the desired position within the bone. Similarly to the outer sleeve 116, when a distal face of the outer sleeve 316 abuts the near cortex of the bone 30, the abutment between the outer sleeve 316 and the bone 30 provides tactile feedback to the user indicating that the headless screw 304 is inserted in the desired position within the bone 30. In addition to the tactile feedback indicating the desired position of the headless screw 304, the insertion device 302 provides an audible feedback as well, as will be described in further detail below.

Figure 16:
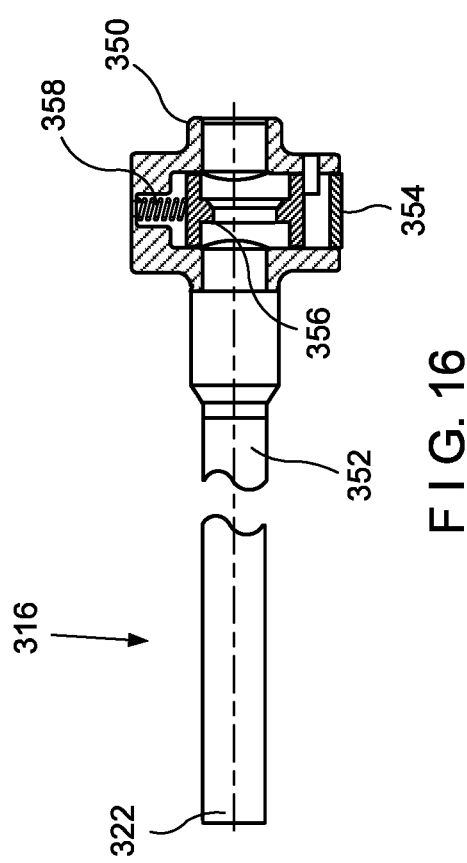
FIG. 16 shows a partial cross-sectional of a side view of an outer sleeve according to the system of FIG. 14.
Figure 17:
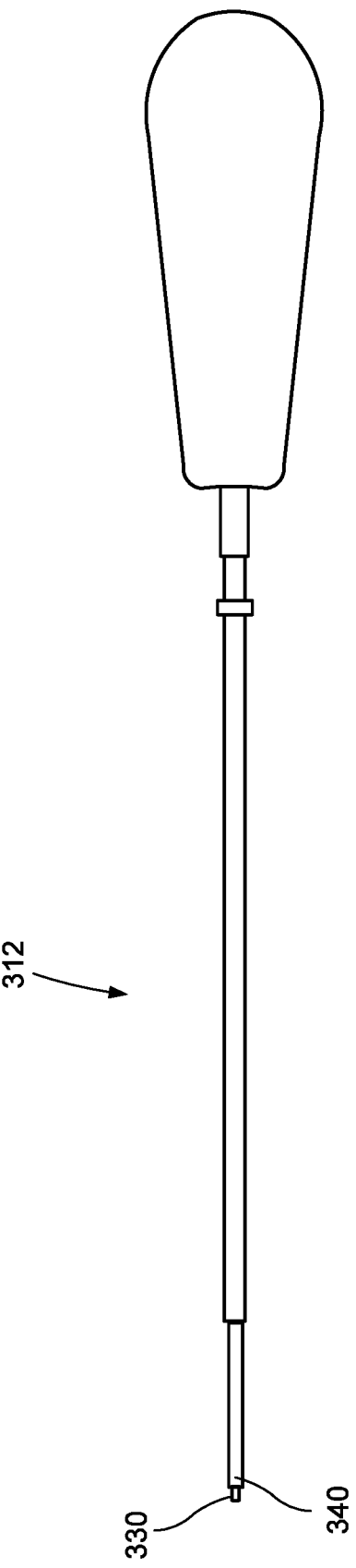
FIG. 17 shows a side view of a driving member according to the system of FIG. 14.

The headless screw 304 is substantially similar to the headless screw 104, as described above with respect to the system 100. The outer sleeve 316, as shown in FIG. 16, is also substantially similarly to the outer sleeve 116, the outer sleeve 316 extending from a proximal end 350 to a distal end 322 and includes a channel 352 extending therethrough. The outer sleeve 116 also includes a locking mechanism 354 at the proximal end 350, including a locking tab 356 biased toward a locked configuration via a biasing element 358. As shown in FIG. 17, the driving member 312 is substantially similar to the driving member 112 and is configured to extend longitudinally through the channel 352 of the outer sleeve 316 and is longitudinally and rotationally movable relative thereto to drive the headless screw 304 into the bone 30 via an engaging portion 330 at a distal end 340 thereof. In a further configuration, the driving member 312 may have a channel extending therethough configured to accommodate a retaining member (not shown), the retaining member being substantially similar to the retaining member 114 shown in FIG. 5.

Similarly to the insertion device 102, the locking tab 356 of the locking mechanism 354 engages a first groove 360 of the driving member 312 in the first position and a second groove 362 of the driving member 312 in the second position. In this embodiment, however, the insertion device 302 is moved from the first position (FIG. 14) toward the second position (FIG. 15) as the headless screw 304 is driven into the bone toward the desired configuration. In particular, the locking tab 356 is moved from the first groove 360 toward the second groove 362 as the headless screw 304 is driven into the desired position within the bone.

In this embodiment, a ramped surface 370 extends between the first and second grooves 360, 362. The ramped surface 370 increases in diameter from a distal end 372 connected to the first groove 360 to a proximal end 374 proximate the second groove 362. The distal end 372 has substantially the same diameter as the first groove 360 while the proximal end 374 has a larger diameter than the second groove 362. Thus, as the driving member 312 is moved distally relative to the outer sleeve 316 to drive the headless screw 304 into the bone, the locking tab 356 slides from the first groove 360 along the ramped surface 370, a biasing element of the locking mechanism 354 compressing as the locking tab 356 slides along the ramped surface 370 until the locking tab 356 is moved proximally past the proximal end 374 of the ramped surface 370 to be received within the second groove 362.

As the locking tab 356 moves proximally past the proximal end 374 of the ramped surface 370, the locking tab 356 reverts to its biased configuration so that the locking tab "clicks" into the second groove 362, providing an audible feedback to the user. The audible feedback indicates to the use that the headless screw 304 has been fully inserted into the bone in the desired configuration so that the proximal face 307 of the headless screw 304 is substantially flush with a surface of the bone 30.

Figure 18:
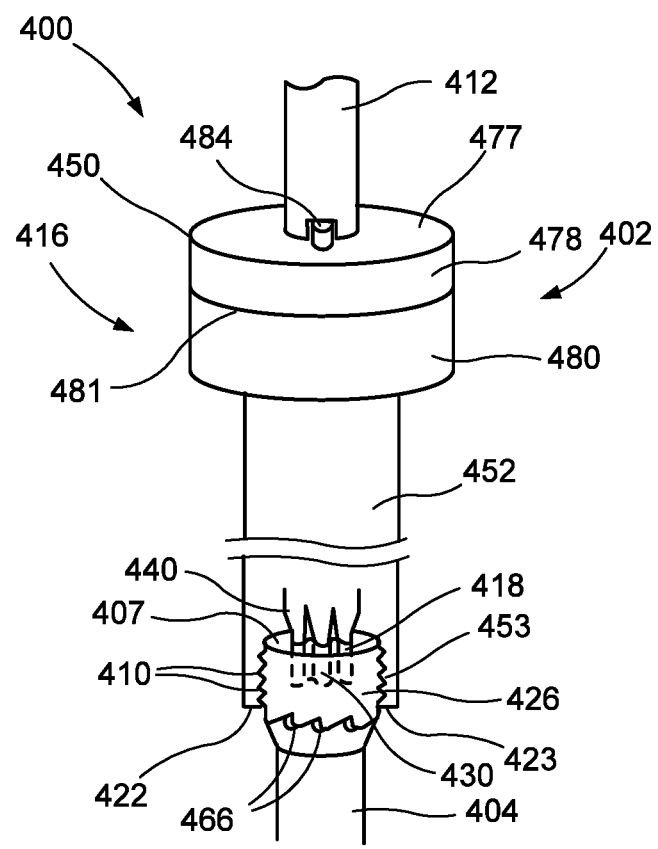
FIG. 18 shows a perspective view of a system according to yet another exemplary embodiment of the present disclosure.
Figure 19:
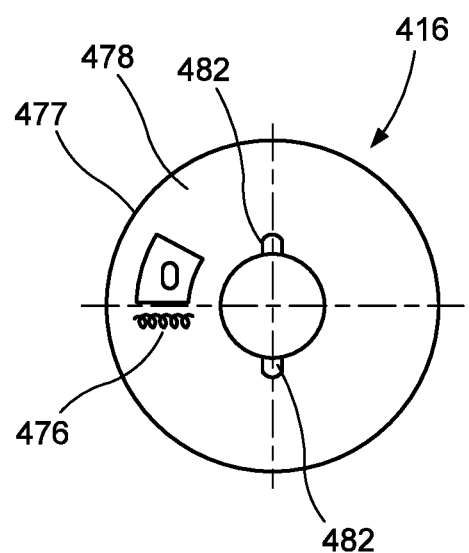
FIG. 19 shows a plan view from a proximal end of an outer sleeve according to the system of FIG. 18.

As shown in FIGS. 18-19, a system 400 according to another exemplary embodiment may be substantially similar to the systems 100-300 described above, comprising an insertion device 402 for driving a headless screw 404 into a desired position within a bone. The insertion device 402 includes a driving member 412 extending through an outer sleeve 416. Rather than including a separate retaining member, however, the outer sleeve 416, in this embodiment, includes a threading 453 along a distal end of a channel 452 extending therethrough for engaging threading 410 along a proximal portion 426 of the headless screw 404 to retain the screw 404 while the screw 404 is being driven into the bone. In addition, the outer sleeve 416 includes a depth indicator 476 for indicating a depth of insertion of the proximal portion of the 426 of the headless screw 404 so that the user may drive the headless screw 404 to the desired position within the bone—e.g., so that a proximal face 407 of the screw 404 is flush to the bone.

Similarly to the outer sleeves 116-316, the outer sleeve 416 extends from a proximal end 450 to a distal end 422 and includes the channel 452 extending therethrough. The outer sleeve 416, however, further includes a proximal portion 478 and a distal portion 480, which have a friction interface 481 such as, for example, a ratchet mechanism. The channel 452 extends through both the proximal and distal portions 478, 480. As described above, the channel 452 includes a distal threaded portion 453 for engaging and retaining the headless screw 404 during insertion of the screw 404 into the bone. Similarly to the outer sleeve 216, a distal face 423 of the outer sleeve 416 includes teeth 466 or other gripping features configured to grip or engage the bone when the outer sleeve 416 is pressed distally thereagainst.

As shown in FIG. 19, the proximal portion 478 includes the depth indicator 476 along a proximal surface 477 so that the depth indicator 476 is visible to a user of the insertion device 402. The depth indicator 476 indicates to the user a depth of insertion of the proximal portion 426 of the headless screw 404. It will be understood by those of skill in the art that a length of the proximal portion 426 of the headless screw 404 would be known to the user of the device 402.

For example, in one embodiment, the proximal portion 426 of the headless screw 404 may have a length of approximately 6.25 mm so that when the depth indicator shows a corresponding depth of insertion, the user will know that the headless screw 404 has been fully countersunk. As will be described in further detail below, the proximal portion 478 also includes a mating feature 482, which is sized and shaped to mate with a corresponding mating feature 484 of the driving member 412 so that, when the mating features 482, 484 engage one another, the proximal portion 478 and the driving member 412 are keyed to one another so that the proximal portion 478 and the driving member 412 are non-rotatable relative to one another.

The driving member 412 is substantially similar to the driving members described above, including an engaging portion 430 at a distal end 440 thereof for engaging a driving recess 418 of the headless screw 404. The driving member 412 extends through the channel 452 of the outer sleeve 416 and includes the mating feature 484 so that when the mating feature 484 engages the mating feature 482 of the proximal portion 478 of the outer sleeve 416, the proximal portion 478 and the driving member 412 are keyed to one another. In one embodiment, the mating feature 482 of the proximal portion 478 may include a longitudinal groove extending along a surface of a portion of the channel extending therethrough while the corresponding mating feature 484 of the driving shaft 412 includes a correspondingly sized and shaped protrusion extending outward from the driving shaft 412 to be received within and slidable along the longitudinal groove of the mating feature 482. It will be understood by those of skill in the art that the mating features 482, 484 may have any of a variety of configurations so long as the mating features 482, 484 key the driving member 412 and the proximal portion 478 relative to one another to prevent rotation of the driving member 412 relative to the proximal portion 478 while also permitting a distal movement of the driving member 412 relative thereto.

In user, the headless screw 404 is assembled with the insertion device 402 prior to insertion. In particular, the outer sleeve 416 is threaded over the proximal portion 426 of the headless screw 404 and the engaging portion 430 of the driving member 412 is inserted into the correspondingly sized and shaped driving recess 418 of the headless screw 404. The headless screw 404 is then inserted into a body and positioned over a target area of the bone. The driving member 412 is then rotated to drive the headless screw 404 into the bone. Since the driving member 412 is keyed to the proximal portion 478 of the outer sleeve 416, rotation of the driving member 412 also causes a rotation of the proximal portion 478. In addition, since the proximal portion 478 and the distal portion 480 of the outer sleeve 416 have a frictional interface, the distal portion 480 is also correspondingly rotated along with the driving member 412 until the outer sleeve 416 is pressed distally against the surface of the bone.

Once the headless screw 404 has been driven far enough into the bone such that the outer sleeve 416 is pressed against the bone, the teeth 466 along the distal face 423 thereof the bone to prevent any further rotation of the distal portion 480 of the outer sleeve 416. Thus, as the user continues to rotate the driving member 412 to drive the headless screw 404 further into the bone, the ratchet mechanism between the proximal and distal portions 478, 480 is engaged, providing an audible feedback to the user as the proximal portion 478 rotates relative to the distal portion 480. The audible feedback indicates that countersinking, driving of the proximal portion 426 of the headless screw 404 into the bone, has begun.

In one embodiment, when the distal face 423 of the outer sleeve 416 first contacts the bone, the depth indicator 476 may indicate an insertion of 0 mm. As the user continues to rotate the driving member 412, however, the proximal portion 478 of the outer sleeve 416 also rotates relative to the distal portion 480 providing audible feedback while the depth indicator 476 shows how far the screw 404 has traveled. As the headless screw 404 is driven further into the bone, the headless screw 404 is also being unthreaded from the threaded distal portion 453 of the outer sleeve 416. Once the depth indicator 476 indicates that the desired depth of insertion has been achieved—i.e., a desired length of the proximal portion 426 of the headless screw 404 has been inserted into the bone—the user may remove the insertion device 402 from the body, leaving the headless screw 404 implanted in the bone in the desired position.

It will be understood by those of skill in the art that modifications and variations may be made in the structure and methodology of the present invention, without departing from the spirit and scope of the invention. Thus, it is intended that the present invention cover the modifications and variations of this invention, provided that they come within the scope of the appended claims and their equivalents.

What is claimed is:

1. A system for treating a bone, comprising:
   a headless screw extending from a proximal end to a distal end and including a threading extending along an outer surface thereof, the headless screw including a driving recess extending into the proximal end thereof; and
   an insertion device including an outer sleeve extending from a proximal end to a distal end and including a channel extending therethrough, a driving member extending longitudinally through the channel of the outer sleeve from a proximal end to a distal end, the proximal end of the driving member extending proximally of the proximal end of the outer sleeve to a distal end configured to engage the driving recess of the headless screw to rotationally drive the headless screw into a bone, the outer sleeve movable relative to the driving member between a first position, in which the distal end of the outer sleeve extends over and covers a proximal portion of the headless screw when the headless screw is engaged with the driving member in an operative configuration, to a second position, in which a distal end of the outer sleeve is longitudinally aligned with a proximal end of the headless screw,
   wherein the outer sleeve includes a locking mechanism for locking the outer sleeve relative to the driving member in one of the first and second positions, the locking mechanism including a locking tab biased toward a locking configuration via a biasing element and a push button compressing the biasing element to move the locking tab toward an unlocked configuration.

2. The system of claim 1, wherein the headless screw further includes a retaining recess extending distally from the driving recess.

3. The system of claim 2, wherein the insertion device further includes a retaining member extending longitudinally through a channel of the driving member from a proximal end to a distal end configured to engage the retaining recess so that the headless screw is retained on the insertion device during insertion of the headless screw into the bone.

4. The system of claim 3, wherein the retaining recess includes a threading therealong and the distal end of the retaining member is correspondingly threaded so that, rotation of the retaining member about a longitudinal axis thereof relative to the driving member, engages the threading of the retaining member with the threading of the retaining recess to retain the headless screw on the insertion device.

5. The system of claim 4, wherein the proximal end of the retaining member includes a knob extending proximal of the proximal end of the driving member to rotate the retaining member relative to the driving member.

6. The system of claim 1, wherein the driving member includes a first groove extending into an outer surface of the driving member so that when the locking tab is received within the first groove the outer sleeve is in the first position relative to driving member, and a second groove extending into the outer surface of the driving member proximal of the first groove so that when the locking tab is received within the second groove the outer sleeve is in the second position relative to the driving member.

7. The system of claim 1, wherein a core diameter of the proximal portion of the headless screw is larger than a core diameter along a remaining portion of the headless screw.

8. The system of claim 1, wherein the outer sleeve includes gripping features extending distally from the distal end thereof, the gripping features configured to engage the bone.

9. The system of claim 1, wherein the outer sleeve includes a threading along the distal end thereof configured to engage a corresponding threading along the proximal portion of the headless screw.

10. The system of claim 9, wherein the outer sleeve includes a proximal portion and a distal portion connected to one another via a friction interface, the distal portion being rotatable about a longitudinal axis thereof.

11. The system of claim 10, wherein the proximal portion of the outer sleeve includes a mating feature configured to mate with a corresponding mating feature on the driving member to prevent the proximal portion from rotating relative to the driving member.

12. The system of claim 10, wherein the proximal portion of the outer sleeve includes a depth indicator that indicates a depth to which the headless screw has been inserted into the bone.

13. A bone screw insertion system, comprising:
   an outer sleeve extending from a proximal end to a distal end and including a channel extending therethrough; and
   a driving member extending longitudinally through the channel of the outer sleeve from a proximal end to a distal end configured to engage a driving recess of a bone screw, the outer sleeve movable relative to the driving member between a first position in which the distal end of the outer sleeve extends over and covers a proximal portion of a bone screw engaged with the driving member, to a second position in which the distal end of the outer sleeve is longitudinally aligned with a proximal end of a bone screw engaged with the driving member,
   wherein the outer sleeve includes a locking mechanism for locking the outer sleeve relative to the driving member in one of the first and second positions, the locking mechanism including a locking tab biased toward a locking configuration via a biasing element and a push button compressing the biasing element to move the locking tab toward an unlocked configuration.

14. The system of claim 13, further comprising a retaining member extending longitudinally through the channel of the driving member from a proximal end to a distal end, the retaining member being configured to releasably engage a retaining recess of a bone screw.

15. The system of claim 14, wherein the distal end of the retaining member is threaded to engage a corresponding threading of the retaining recess.

16. The system of claim 15, wherein the proximal end of the retaining member includes a knob extending proximal of the proximal end of the driving member to rotate the retaining member relative to the driving member.

17. The system of claim 13, wherein the driving member includes a first groove extending into an outer surface of the driving member so that when the locking tab is received within the first groove the outer sleeve is in the first position relative to driving member, and a second groove extending into the outer surface of the driving member proximal of the first groove so that when the locking tab is received within the second groove the outer sleeve is in the second position relative to the driving member.

18. The system of claim 13, wherein the outer sleeve includes gripping features extending distally from the distal end thereof, the gripping features configured to engage the bone.

19. The system of claim 13, wherein the outer sleeve includes a threading along an inner surface of a distal portion thereof configured to engage a corresponding threading along the proximal portion of a headless screw received within the outer sleeve.

20. The system of claim 19, wherein the outer sleeve includes a proximal portion and a distal portion connected to one another via a friction interface, the distal portion of the outer sleeve being rotatable about a longitudinal axis thereof relative to the proximal portion of the outer sleeve.

21. The system of claim 20, wherein the proximal portion of the outer sleeve includes a mating feature configured to mate with a corresponding mating feature on the driving member to prevent the proximal portion from rotating relative to the driving member.

22. The system of claim 20, wherein the proximal portion of the outer sleeve includes a depth indicator that indicates a depth to which the headless screw engaged to the driving member has been inserted into the bone.

* * * * *